United States Patent
Merkel et al.

(10) Patent No.: US 9,676,687 B2
(45) Date of Patent: Jun. 13, 2017

(54) FLUORINATION PROCESS AND REACTOR

(71) Applicant: Honeywell International, Inc., Morristown, NJ (US)

(72) Inventors: Daniel C. Merkel, Orchard Park, NY (US); Hsueh Sung Tung, Getzville, NY (US); Haiyou Wang, Amherst, NY (US); Haluk Kopkalli, Staten Island, NY (US); Yuon Chiu, Denville, NJ (US)

(73) Assignee: HONEYWELL INTERNATIONAL. INC., Morristown, NJ (US)

( * ) Notice: Subject to any disclaimer, the term of this patent is extended or adjusted under 35 U.S.C. 154(b) by 0 days.

(21) Appl. No.: 15/139,778

(22) Filed: Apr. 27, 2016

(65) Prior Publication Data

US 2016/0237010 A1    Aug. 18, 2016

Related U.S. Application Data

(62) Division of application No. 14/206,088, filed on Mar. 12, 2014, now Pat. No. 9,353,029.

(60) Provisional application No. 61/783,545, filed on Mar. 14, 2013.

(51) Int. Cl.
    *C07C 17/25*    (2006.01)
    *C07C 17/20*    (2006.01)
    *C07C 21/18*    (2006.01)
    *B01J 19/24*    (2006.01)
    *B01J 4/00*     (2006.01)

(52) U.S. Cl.
    CPC .............. *C07C 17/25* (2013.01); *B01J 4/002* (2013.01); *B01J 19/24* (2013.01); *C07C 17/206* (2013.01)

(58) Field of Classification Search
    CPC ....... C07C 17/25; C07C 17/206; C07C 21/18; C07C 17/42; C07C 17/06; C07C 17/20; B01J 8/0285
    USPC ................................................. 570/156, 160
    See application file for complete search history.

(56) References Cited

U.S. PATENT DOCUMENTS

| | | |
|---|---|---|
| 3,284,169 A | 11/1966 | Tominaga et al. |
| 5,710,352 A | 1/1998 | Tung |
| 6,045,772 A | 4/2000 | Szydlowski et al. |
| 6,660,130 B2 | 12/2003 | Scott et al. |
| 8,445,736 B2 | 5/2013 | Elsheikh et al. |
| 2001/0012910 A1 | 8/2001 | Scott et al. |
| 2005/0256348 A1 | 11/2005 | Wilmet et al. |
| 2008/0045758 A1 | 2/2008 | Cohn et al. |
| 2008/0154072 A1 | 6/2008 | Owens et al. |
| 2008/0274277 A1 | 11/2008 | Rashidi et al. |
| 2009/0030244 A1 | 1/2009 | Merkel et al. |
| 2010/0036179 A1* | 2/2010 | Merkel ................. C07C 17/087 570/156 |
| 2010/0233057 A1 | 9/2010 | Luly et al. |
| 2010/0331583 A1 | 12/2010 | Johnson et al. |
| 2011/0087054 A1 | 4/2011 | Tirtowidjojo et al. |
| 2011/0087056 A1 | 4/2011 | Tirtowidjojo et al. |
| 2012/0005337 A1 | 1/2012 | Sokabe et al. |
| 2012/0022303 A1 | 1/2012 | Nose et al. |
| 2012/0078020 A1 | 3/2012 | Elsheikh et al. |
| 2012/0184785 A1 | 7/2012 | Cottrell et al. |

FOREIGN PATENT DOCUMENTS

| | | |
|---|---|---|
| CN | 101874009 A | 10/2010 |
| CN | 102686543 A | 9/2012 |
| EP | 1 837 306 A1 | 6/2007 |
| WO | 94/23813 A1 | 10/1994 |
| WO | 9423813 | 10/1994 |
| WO | 2008054781 A1 | 5/2008 |
| WO | 2009015317 A1 | 11/2009 |
| WO | 2009158321 A1 | 12/2009 |
| WO | 2012057367 A1 | 5/2012 |
| WO | 2012/099776 A1 | 7/2012 |
| WO | 2012099766 A1 | 7/2012 |

OTHER PUBLICATIONS

International Search Report and Written Opinion corresponding to PCT/US2014/025551, dated Jul. 17, 2014.
International Search Report corresponding to PCT/US2014/025551, dated Jul. 9, 2015.
Partial European Search Report dated Jul. 8, 2015 issued in Application No. 14773146.7.
First Office Action issued in Chinese Patent Application No. 2014800149071 dated Jun. 6, 2016 (in English and Chinese).
Extended European Search Report dated Dec. 19, 2016 received in a corresponding foreign application.

* cited by examiner

*Primary Examiner* — Jafar Parsa
(74) *Attorney, Agent, or Firm* — Scully, Scott, Murphy & Presser, P.C.

(57) ABSTRACT

The invention relates to a process to prepare tetrahalopropenes, such as 2-chloro-3,3,3-trifluoropropene (1233xf). The process comprises atomizing a feed material, such as 1,1,2,3-tetrachloropropene (1230xa) and the like, and mixing it with superheated HF to form a vaporized composition of feed material and HF with substantially instantaneous contact with a vapor phase fluorination catalyst. The invention extends catalyst life and forestalls catalyst deactivation.

8 Claims, 1 Drawing Sheet

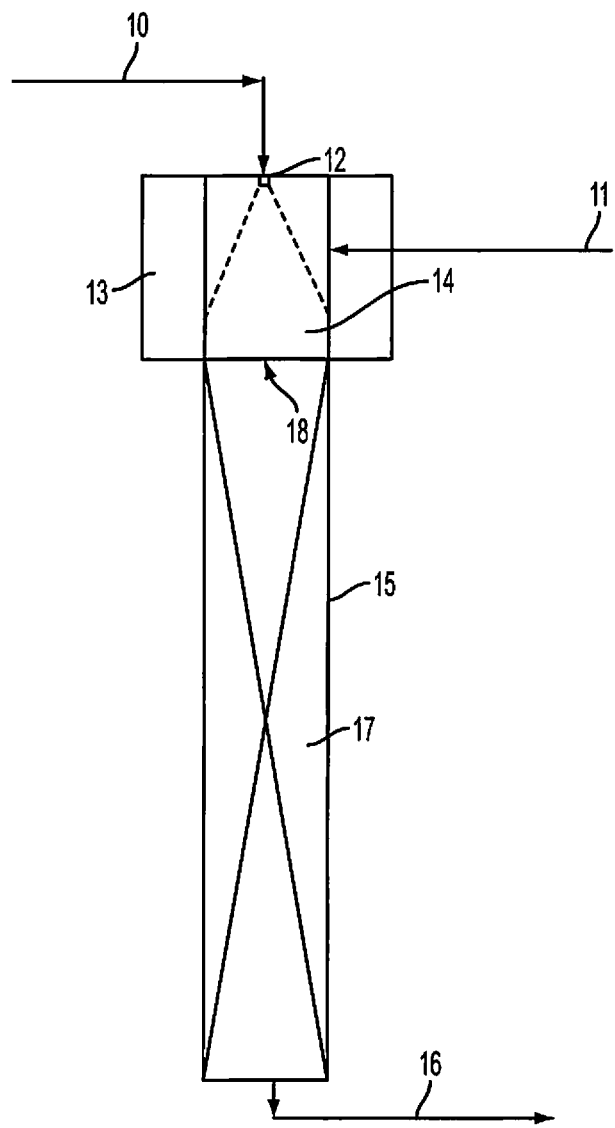

FLUORINATION PROCESS AND REACTOR

This application is a divisional application claiming priority under 35 U.S.C. 121 to U.S. Ser. No. 14/206,088 filed Mar. 12, 2014, a notice of allowance in which issued on Jan. 28, 2016, which claims priority under 35 U.S.C. 119 to provisional application U.S. Ser. No. 61/783,545 filed Mar. 14, 2013, the entire contents of all the foregoing being incorporated herein by reference.

FIELD OF THE INVENTION

The invention relates to a reactor design particularly useful in preparing fluorinated organic compounds, including without limitation, in methods for preparing fluorinated olefins, such as 2,3,3,3-tetrafluoropropene (HFO-1234yf).

BACKGROUND OF THE INVENTION

Hydrofluoroolefins (HFOs), such as tetrafluoropropenes (including 2,3,3,3-tetrafluoropropene (HFO-1234yf), are now known to be effective refrigerants, heat transfer media, propellants, foaming agents, blowing agents, gaseous dielectrics, sterilants carriers, polymerization media, particulate removal fluids, carrier fluids, buffing abrasive agents, displacement drying agents and power cycle working fluids, chemical intermediates, monomers and the like. Unlike chlorofluorocarbons (CFCs) and hydrochlorofluorocarbons (HCFCs), both of which potentially damage the Earth's ozone layer, HFOs do not contain chlorine and, thus, pose no threat to the ozone layer. HFO-1234yf has also been shown to be a low global warming compound with low toxicity and, hence, can meet increasingly stringent requirements for refrigerants in mobile air conditioning. Accordingly, compositions containing HFO-1234yf are among the materials being developed for use in many of the aforementioned applications.

Some HFOs are prepared by multiple steps that involve fluorinating a chlorinated organic compound with a fluorination agent such as hydrogen fluoride in the presence of a fluorination catalyst. These reactions may be conducted in either the liquid or gas phase or a combination of these. In one process to manufacture HFO-1234yf (2,3,3,3-tetrafluoropropene), the following reaction sequence is known:

Step 1: TCP+3HF→1233xf+3HCl wherein TCP (also known as 1230xa) is 1,1,2,3-tetrachloropropene, or $CCl_2=CClCH_2Cl$; and 1233xf is 2-chloro-3,3,3,-trifluoropropene, or $CH_2=CClCF_3$. Step (1) preferably occurs in the vapor phase reactor charged with a solid catalyst, preferably a fluorination catalyst, e.g. chromium oxide ($Cr_2O_3$) and the like as known in the art.

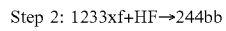

Step 2: 1233xf+HF→244bb wherein 244bb is 2-chloro-1,1,1,2-tetrafluoropropane, or $CH_3CClFCF_3$. Step (2) preferably occurs in a liquid phase reactor charged with a liquid catalyst. A by-product of Step 2 can also form as follows: 1233xf+2HF→245cb+HCl, where 245cb is 1,1,1,2,2-pentafluoropropane, or $CH_3CF_2CF_3$;

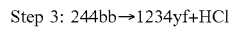

Step 3: 244bb→1234yf+HCl wherein 1234yf is 2,3,3,3-tetrafluoropropene, or $CH_2=CFCF_3$. Step (3) preferably occurs in a vapor phase reactor with a dehydrochlorination catalyst.

It has been found that while the catalyst used in Step (1) is quite active and selective, it nonetheless tends to deactivate (lose activity), slowly during the reaction. Among other things, it has been theorized that often in the course of known protocols, when TCP is heated and vaporized (including preferably in the presence of anhydrous hydrogen fluoride (AHF)) undesired reactions occur. It is believed these include the formation of oligomers, polymers, and decomposition products ($C_1$ and $C_2$ carbon-containing compounds) which can further lead to coking of the catalyst. Thus, formation of these compounds is thought to lead directly to catalyst deactivation. Deactivation of the catalyst compromises yield and creates other economic disadvantages and disruption to the process.

Therefore, a need exists to extend catalyst life for the conversion of 1230xa to 1233xf.

SUMMARY OF THE INVENTION

The present invention is, in part, related to a process involving a particular introduction methodology for TCP into the reaction zone of the fluorination reactor that minimizes the undesired TCP side reactions and decomposition which will lead to longer catalyst stability. The present invention provides a means to reduce the residence time that TCP is heated and vaporized while minimizing the amount of time that TCP and anhydrous hydrogen fluoride (AHF) are in contact with each other before they are introduced into the reaction zone. By reducing these times the formation of oligomers, polymers, and decomposition products that cause catalyst deactivation is also minimized.

In one embodiment, the invention relates to a reactor apparatus design that allows for TCP to be fed as a liquid at ambient temperature where it is known to be stable. The liquid TCP is fed into a heated zone directly above the catalyst bed (for a down flow reactor; for an up flow reactor, the TCP is fed below the catalyst bed through a fine nozzle that atomizes the TCP and/or creates a TCP mist. Separately, a superheated AHF gaseous stream is also fed into the heated zone above (or below) the catalyst bed, but through a different nozzle than the TCP. The temperature of the heated zone, in combination with the heat provided by the superheated AHF gas, which will be at least the desired reaction temperature, provide sufficient heat to substantially immediately vaporize the atomized TCP feed. The now gaseous mixture is substantially almost instantaneously enters the catalyst bed where the fluorination reaction occurs. Because of the preferably close proximity of the TCP feed nozzle to the catalyst bed, the contact time for TCP and AHF, before reaction, is at a minimum, which in turn minimizes the formation of oligomers, polymers, and decomposition products that cause catalyst deactivation. Feed materials, other than TCP, including e.g. 240db and 2,3,3,3-tetrachloropropene are also contemplated.

In another embodiment, the present invention relates to an improved method for producing a tetrahalopropene, such as 2-chloro-3,3,3,-trifluoropropene (1233xf), that involves reacting one chlorocarbon or mixed chlorocarbon feed material, e.g. selected from the group consisting of 1,1,2,3-tetrachloropropene, 1,14,2,3-pentachloropropane (HCC-240db), and 2,3,3,3-tetrachloropropene with hydrogen fluoride, and the like and combinations thereof, in a vapor phase reaction vessel and in the presence of a vapor phase fluorination catalyst at conditions effective to produce the desired tetrahalopropene.

In a preferred practice, the contacting step produces a reaction product comprising a tetrahalopropene, and in particular 2-chloro-3,3,3-trifluoropropene (HFO-1233xf). In preferred embodiments, the contacting step comprises reacting a tetrachloropropene and/or pentachloropropane with a fluorinating agent, such as HF, in the gas phase in the presence of at least one catalyst. In a particularly preferred embodiment, the catalyst is $Cr_2O_3$.

In certain preferred embodiments, the conversion of the tetrachloropropene is greater than about 70%, preferably from about 70% to about 100%, preferably between about 85% and about 100%, more preferably between about 95% to about 99%; and the selectivity for HFO-1233xf is greater than about 50%, preferably between about 70% and about 99%, more preferably between about 90% to about 99%. The practice of the invention in conjunction with the catalyst component results in a significant improvement in catalyst longevity. In certain embodiments, catalyst performance is improved by at least 20%, more preferably by at least 40%, as opposed to reactions conducted with catalyst where a high boiling chlorocarbon feed material is heated and/or vaporized and/or when said heated and/or vaporized high boiling chlorocarbon feed material is contacted with anhydrous hydrogen fluoride for a relatively long length of time as typified in the art. The practice of the invention results in a process that is significantly more efficient and cost-effective than those typically known heretofore insofar as it enable use of reduced catalyst amounts and results in greater conversion of starting materials to the desired product. It has been found that the use of the present invention in conjunction with the catalyst component results in a significant improvement in catalyst longevity In another embodiment, the invention relates to reactor apparatus comprising a reaction chamber; a heating chamber disposed on the reaction chamber, the heating chamber comprising a mixing area in fluid communication with said reaction chamber; at least first and second feed lines in fluid communication with said mixing area; and an atomizing nozzle disposed on at least said first feed line, said nozzle having an exit into said mixing area.

In another embodiment, the invention relates to process to prepare a tetrahalopropene comprising: a) providing a reactor apparatus having a catalyst bed within a reaction chamber, and a heating chamber disposed on the reaction chamber, the heating chamber comprising a mixing area in fluid communication with said reaction chamber; b) supplying superheated HF and an atomized feed material selected from the group consisting of chlorocarbons, mixed chlorocarbons, and combinations thereof, to the mixing area under conditions effective to form a vaporized composition comprising the feed material and the HF; and c) contacting the vaporized composition with the catalyst bed under conditions effective to form the tetrahalopropene, wherein the contacting occurs substantially instantaneously with the formation of the vaporized composition.

In another embodiment, the invention relates to process to prepare 2-chloro-3,3,3-trifluoropropene (1233xf) comprising a) mixing superheated HF and atomized feed material selected from the group consisting of 1,1,2,3-tetrachloropropene (1230xa), 1,1,1,2,3-tetrachloropropane (HCC-240db), 2,3,3,3-tetrachloropropene (1230xf), and combinations thereof, under conditions effective to form a vaporized composition comprising the feed material and the HF; and b) contacting the vaporized composition with a catalyst under conditions to form 1233xf, the contacting preferably occurring substantially instantaneously with the formation of the vaporized composition.

BRIEF DESCRIPTION OF THE FIGURE

The FIGURE depicts a reactor design of the present invention.

DETAILED DESCRIPTION OF THE INVENTION

The foregoing summary and general description of the invention and the ensuing detailed description are exemplary and explanatory and are not restrictive of the invention, as defined in the appended claims. Other features and embodiments and modifications will be apparent from the present description and are within the scope of the invention. The entire contents of U.S. Pat. Nos. 8,258,355, 8,084,653, and US Published Patent Application No. 2007/0197842 are incorporated herein by reference.

In one embodiment, the present invention enables the production of desirable haloolefins, preferably $C_3$ haloolefins; more preferably, the production of $C_3$ haloolefins using the combination of at least one catalyst and utilizing the reactor design described herein.

In one embodiment, 1,1,2,3-tetrachloropropene, 2,3,3,3-tetrachloropropene, or 1,1,1,2,3-pentachloropropane or mixtures thereof, is exposed to reaction conditions to produce a reaction product comprising 2-chloro-3,3,3,-trifluoropropene.

In one embodiment the process of present invention preferably comprises reacting one or more chlorocarbon or mixed chlorocarbon feed material for example as selected from the group consisting of 1,1,2,3-tetrachloropropene (1230xa), 1,1,1,2,3-pentachloropropane (HCC-240db), and 2,3,3,3-tetrachloropropene (1230xf) and the like, with a fluorinating agent, such as anhydrous HF, to produce a fluorinated haloolefin, preferably a $C_3$ fluorinated haloolefin, more preferably 2-chloro-3,3,3,trifluoropropene (HFC-1233xf). This preferred reaction step may be described, by way of illustration but not necessarily by way of limitation, by the following reaction equation in connection with embodiments in which the tetrachloropropene is 1,1,2,3-tetrachloropropene and the fluorinating agent is hydrogen fluoride:

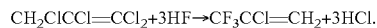

$$CH_2ClCCl=CCl_2+3HF \rightarrow CF_3CCl=CH_2+3HCl.$$

In certain preferred embodiments, the present converting step is carried out under conditions effective to provide a tetrachloropropene conversion of at least about 40%, more preferably at least about 55%, and even more preferably at least about 70%. In certain preferred embodiments the conversion is at least about 90%, and more preferably about 100%.

Further in certain preferred embodiments, the conversion of the tetrachloroproene to produce a $C_3$ haloolefin is conducted under conditions effective to provide a $C_3$ haloolefin selectivity of at leak about 85%, more preferably at least about 90%, and more preferably at least about 95%, and even more preferably about 100%.

In a particularly preferred embodiment, the invention relates to a continuous method for producing 2-chloro-3,3,3,-trifluoropropene (HCFC-1233xf) by vapor phase fluorination of one chlorocarbon or mixed chlorocarbon feed material selected from the group of 1,1,1,2,3-pentachloropropane (HCC-240db), 2,3,3,3-tetrachloropropene (1230xf), and 1,1,2,3,-tetrachloropropene (HCC-1230xa) with hydrogen fluoride to produce a stream comprising hydrogen fluoride, 2-chloro-3,3,3,-trifluoropropene and hydrogen chloride.

This reaction may be conducted in any reactor suitable for a vapor or liquid phase fluorination reaction. Preferably the reactor is constructed from materials which are resistant to the corrosive effects of hydrogen fluoride and catalyst such as Hastalloy, Inconel, Monel and vessels lined with fluoropolymers. In case of a vapor phase process, the reactor is filled with a vapor phase fluorination catalyst. Any fluorination catalysts known in the art may be used in this process. Suitable catalysts include, but are not limited to chromium, aluminum, cobalt, manganese, nickel and iron oxides, hydroxides, halides, oxyhalides, inorganic salts thereof and their mixtures. Combinations of catalysts suitable for the present invention nonexclusively include $Cr_2O_3$, $FeCl_3/C$, $Cr_2O_3/Al_2O_3$, $Cr_2O_3/AlF_3$, $Cr_2O_3/carbon$, $CoCl_2/Cr_2O_3/Al_2O_3$, $NiCl_2/Cr_2O_3/Al_2O_3$, $CoCl_2/AlF_3$, $NiCl_2/AlF_3$ and mixtures thereof. Chromium oxide/aluminum oxide catalysts are described in U.S. Pat. No. 5,155,082 which is incorporated herein by reference. Chromium (III) oxides such as crystalline chromium oxide or amorphous chromium oxide are preferred with amorphous chromium oxide being most preferred. Chromium oxide ($Cr_2O_3$) is a commercially available material which may be purchased in a variety of particle sizes. Fluorination catalysts having a purity of at least 98% are preferred. The fluorination catalyst is present in an excess but in at least an amount sufficient to drive the reaction.

In one embodiment, the reactor is preheated to the fluorination reaction temperature while anhydrous HF is fed to the reactor. The stream containing the chlorocarbon feed material, for example the 1,1,2,3-tetrachloropropene is introduced into the reaction vessel next, which is maintained at the desired temperature. The 1,1,2,3,-tetrachloropropene (HCC-1230xa) is fed to the reactor as a liquid at temperatures preferably less than about 100° C., more preferably at temperatures less than about 50° C., and even more preferably at ambient temperature. The HF may be fed to the reactor at any convenient temperature and pressure. In a preferred embodiment the HF is pre-vaporized or preheated to a temperature of from about 180° C. to about 350° C. (superheated) prior to entering the reactor. In another embodiment, the HCC-1230xa is vaporized in the reaction vessel after being atomized or made into a fine mist by use of a nozzle. The HF and HCC-1230xa feeds are then adjusted to the desired mole ratio. The HF to HCC-1230xa mole ratio preferably ranges from about 3:1 to about 100:1; more preferably from about 4:1 to about 50:1 and most preferably from about 5:1 to about 20:1.

The vapor phase fluorination reaction is conducted at a preferred temperature ranging from about 80° C. to about 400° C.; more preferably from about 100° C. to about 350° C. and most preferably from about 200° C. to about 330° C. Reactor pressure is not critical and can be superatmospheric, atmospheric or under vacuum. The vacuum pressure can be from about 5 torr (0.0966 psig) to about 760 torr (14.69 psig). During the vapor phase fluorination reaction, HCC-1230xa and HF are reacted in a vapor phase in the presence of the fluorination catalyst. The reactant vapor is allowed to contact the fluorination catalyst for from about 1 to 120 seconds or more preferably from about 1 to 20 seconds. For purposes of this invention, "contact time" is the time required for the gaseous reactants to pass through the catalyst bed assuming that the catalyst bed is 100% void.

In the preferred embodiment, the process flow is in the down direction through a bed of the catalyst. Before each use, the catalyst is preferably dried, pre-treated and activated. It may also be advantageous to periodically regenerate the catalyst after prolonged use while in place in the reactor. Pre-treatment can be done by heating the catalyst to about 250° C. to about 430° C. in a stream of nitrogen or other inert gas. The catalyst may then be activated by treating it with a stream of HF diluted with a large excess of nitrogen gas in order to obtain high catalyst activity. Regeneration of the catalyst may be accomplished by any means known in the art such as, for example, by passing air or air diluted with nitrogen over the catalyst at temperatures of from about 100° C. to about 400° C., preferably from about 200° C. to about 375° C., for from about 8 hours to about 3 days, depending on the size of the reactor.

Thus, it is contemplated that the present reaction may be performed using a wide variety of process parameters and process conditions in view of the overall teachings contained herein. However, it is preferred in certain embodiments that this reaction step comprises a gas phase reaction, preferably in the presence of catalyst.

Referring to the FIGURE, which depicts a preferred embodiment of the invention, reactor apparatus 15 is comprised of heating chamber 13, heated by heating means known in the art, such as steam and the like, within which is mixing area 14. Apparatus 15 is further comprised of catalyst bed 17 which commences at boundary 18 and demarcates the start of the reaction zone. TCP, at about ambient temperature, is fed through feed line 10 and is introduced into mixing area 14 via nozzle 12 which is configured to atomize the TCP. Anhydrous HF is superheated and fed into mixing area 14 via line 11. The superheated HF and the heat from the heating area is sufficiently hot to almost immediately vaporize the atomized TCP. The now gaseous TCP/HF mixture, which is at least at the desired reaction temperature, almost instantaneously after vaporization enters the catalyst bed 17, at boundary 18, wherein the fluorination reaction occurs. Nozzle 12 is located proximate 18 to minimize the formation of oligomers, polymers, and other decomposition products causative of catalyst deactivation. Fluorinated produce, such as 1233xf, is removed via outlet 16. In the practice of the invention, without limitation to the FIGURE, the HF and feed material, e.g. the TCP, has a residence in the heating chamber of no greater than about 1 sec.; preferably, no greater than about 0.75 sec; more preferably, no greater than about 0.5 sec.

The present reaction also incorporates the use of a fluorination reactor design herein in processes to prepare a tetrahalopropene as herein defined. It has been found that the present invention results in a significant increase to the longevity of the catalyst, e.g. the vapor phase fluorination catalyst, preferably by at least 20%, more preferably by at least 40%. By way of non-limiting explanation, it is believed that the present invention substantially prevents the undesirable polymerization and/or decomposition of the starting materials that form a layer of coke on the catalyst surface.

In another practice the invention may be employed, for example, as part of a larger process to make compounds such as 2,3,3,3-tetrafluoropropene (1234yf). For example, the process of the invention can be the first step of the three-step process to make 1234yf as described above. In a preferred embodiment in this regard, the present invention comprises a step of an integrated manufacturing process for making 2,3,3,3-tetrafluoropropene. The preferred starting material for this process is one or more chlorinated compounds according to Formulae I, II and/or III:

CX$_2$=CCl—CH$_2$X  (Formula I)

CX$_3$—CCl=CH2  (Formula II)

CX$_3$—CHCl—CH$_2$X  (Formula III)

wherein X is independently selected from F, Cl, Br, and I, provided that at least one X is not fluorine; Preferably, these compounds contain at least one chlorine, more preferably a majority of X is chlorine, and even more preferably all X is chlorine. Preferably, the method generally comprises at least three reaction steps.

Step 1:

In the first step, the present invention is employed as described herein to catalytically fluorinate a starting composition including one or more compounds having Formula (I), (II) or (III), preferably 1,1,2,3-tetrachloropropene and/or 2,3,3,3-tetrachloropropene (TCP) and/or 1,1,1,2,3-pentachloropropane (240db) and/or 2,3,3,3-tetrachloropropene, reacts with anhydrous HF in a first vapor phase reactor (fluorination reactor) to produce a mixture of 2-chloro-3,3,3-trifluoropropene (1233xf) and HCl.

Step 2:

In the second step, 1233xf as produced in Step 1, is converted at more than about 95% to 244bb using HF preferably in a liquid phase reactor in the presence of a fluorination catalyst, such as without limitation, those known in the art, and are preferably liquid phase fluorination catalysts. A non-exhaustive list of such fluorination catalysts serviceable in this regard include: Lewis acids, transition metal halides, transition metal oxides, Group IVb metal halides, Group Vb metal halides, or combinations thereof. Non-exclusive examples of liquid phase fluorination catalysts include antimony halide, a tin halide, a tantalum halide, a titanium halide, a niobium halide, and molybdenum halide, an iron halide, a fluorinated chrome halide, or combinations thereof. Specific non-exclusive examples of liquid phase fluorination catalysts are SbCl$_5$, SbCl$_3$, SbF$_5$, SnCl$_4$, TaCl$_5$, TiCl$_4$, NbCl$_5$, MoCl$_6$, FeCl$_3$, a fluorinated species of SbCl$_5$, a fluorinated species of SbCl$_3$, a fluorinated species of SnCl$_4$, a fluorinated species of TaCl$_5$, a fluorinated species of TiCl$_4$, a fluorinated species of NbCl$_5$, a fluorinated species of MoCl$_6$, a fluorinated species of FeCl$_3$, or combinations thereof. Antimony pentachloride, SbCl$_5$, is preferred, with a fluorinated species of SbCl$_5$ more preferred.

Step 3:

In the third step, the 244bb, produced from Step 2, is fed to a second vapor phase reactor (dehydrochlorination reactor) to be dehydrochlorinated to make the desired product 2,3,3,3-tetrafluoropropene (1233yf). This reactor contains a catalyst that can catalytically dehydrochlorinate 244bb to make 1234yf.

The catalysts here may be metal halides, halogenated metal oxides, neutral (or zero oxidation state) metal or metal alloy, or activated carbon in bulk or supported form. When metal halides or metal oxides catalysts are used, preferably mono-, bi-, and tri-valent metal halides, oxide and their mixtures/combinations, and more preferably mono-, and bi-valent metal halides and their mixtures/combinations. Component metals include, but are not limited to, Cr$^{3+}$, Fe$^{3+}$, Mg$^{2+}$, Ca$^{2+}$, Ni$^{2+}$, Zn$^{2+}$, Pd$^{2+}$, Li$^+$, Na$^+$, K$^+$, and Cs$^+$. Component halogens include, but are not limited to, F$^-$, Cl$^-$, Br$^-$, and I$^-$. Examples of useful mono- or bi-valent metal halide include, but are not limited to, LiF, NaF, KF, CsF, MgF$_2$, CaF$_2$, LiCl, NaCl, KCl, and CsCl. Halogenation treatments can include any of those known in the prior art, particularly those that employ HF, F$_2$, HCl, Cl$_2$, HBr, Br$_2$, HI, and I$_2$ as the halogenation source.

When neutral, i.e., zero valent, metals, metal alloys and their mixtures are used. Useful metals include, but are not limited to, Pd, Pt, Rh, Fe, Co, Ni, Cu, Mo, Cr, Mn, and combinations of the foregoing as alloys or mixtures. The catalyst may be supported or unsupported. Useful examples of metal alloys include, but are not limited to, SS 316, Monel 400, Inconel 825, Inconel 600, and Inconel 625.

Preferred catalysts include activated carbon, stainless steel (e.g. SS 316), austenitic nickel-based alloys (e.g. Inconel 625), nickel, fluorinated 10% CsCl/MgO, and 10% CsCl/MgF$_2$. The reaction temperature is preferably about 300-550° C. and the reaction pressure is preferably about 0-150 psig. Preferably, the reactor effluent is fed to a caustic scrubber or to a distillation column to remove the by-product of HCl to produce an acid-free organic product which, optionally, may undergo further purification.

Example 1

This example illustrates the continuous vapor phase fluorination reaction of 1,1,2,3-tetrachloropropene (1230xa) to 2-chloro-3,3,3-trifluoropropene (1233xf). The fluorination catalyst for the experiment was fluorinated Cr$_2$O$_3$.

A continuous vapor phase fluorination reaction system consisting of N$_2$, HF, and organic feed systems, feed vaporizer, superheater, 2 inch ID Monel reactor, acid scrubber, drier, and product collection system was used to study the reaction. The reactor was about 33 inches in length. The reactor was loaded with 1.8 liters of pretreated fluorinated Cr$_2$O$_3$ catalyst. The reactor was then heated to a temperature of about 180° C. with a N$_2$ purge going over the catalyst after the reactor had been installed in a constant temperature sand bath. HF feed was introduced to the reactor (via the vaporizer and superheater) as a co-feed with the N$_2$ for 15 minutes when the N$_2$ flow was stopped. The HF flow rate was adjusted to 1.9 lb/lhr and then 1,1,2,3-tetrachloropropene (1230xa) feed was started to the reactor (via the vaporizer and superheater). The feed rate of 1230xa was kept steady at 1.0 lb/hr and HF feed was kept steady at 1.9 lb/hr for about a 17 to 1 mole ratio of HF to 1230xa. Once the reaction started the catalyst bed temperature rose to about 200° C. The reaction temperature was gradually increased as catalyst deactivation occurred to maintain desired product collection rate, and reaction was stopped once the reaction temperature reached 300° C. and the conversion of 1230xa was <30%. The reaction pressure was kept constant at 70 psig during the entire course of reaction. The reaction was continuously run for only 588 hours before the experiment ended. 192 lb of 1233xf and 1232xf was produced. The average conversion of 1230xa and the average selectivity to 1233xf were 69.4%, and 87.3%, respectively.

The catalyst was then regenerated using oxygen and high temperature to burn off the coke that was coating the surface of the catalyst. The reaction was restarted as before and the catalyst had regained its activity. 1230xa conversion was 100% and 1233xf selectivity was >97% at a catalyst bed hot spot temperature of 200° C. and at a pressure of 70 psig.

Example 2

This example shows that 1230xa forms oligimers upon heating and vaporizing.

After feeding some 99.5 GC area % pure 1230xa through a vaporizer at 180° C. and 70 psig for 24 hours, the vaporizer was cooled and some liquid was drained out of the vaporizer and analyzed by GC and GC/MS. Several dimers were present and the purity of 1230xa was only 97.8%. Likewise, material collected after the vaporizer was analyzed by GC and GC/MS. Several dimers were present and the purity of 1230xa was only 98.6%.

TABLE 1

GC/MS of 1230xa material drained from vaporizer after stability experiment

| Species identified by GC-MS | Drained sample from Run No. 7 70 psig/180° C. |
|---|---|
| G-30[1] | ✓ |
| 1232xf | ✓ |
| 1231 isomers (2) | ✓ |
| Trichloroethene | ✓ |
| Tetrachloropropane | ✓ |
| 1230xa | ✓ |
| Hexachloroethane | ✓ |
| Dimer 1 | ✓ |
| Dimer 2 | ✓ |
| Dimer 3 | ✓ |
| Dimer 4 | ✓ |
| Dimer 5 | ✓ |
| Dimer 6 | ✓ |

[1]Added before phase separation

Example 3

A new reactor design is tried where a fine nozzle tip made of Hastelloy C276 is installed at the top of the reactor and the 1230xa feed line from the 1230xa feed pump is connected directly to it instead of a vaporizer/superheater. On opposite sides of the reactor about 2 inches from the top are 2 separate ports. The HF feed line from the exit of the HF superheater is split and piped to both of the side ports to better distribute the superheated gaseous HF gas feed to the reactor. The reactor is a 2 inch ID×36 inch L Monel pipe reactor and is charged with about 1.3 liters of pretreated fluorinated $Cr_2O_3$ catalyst. This leaves a length of about 8 inches from the top of the catalyst bed to the nozzle that is just empty pipe. The continuous vapor phase fluorination reaction system also consists of $N_2$ and HF feed systems, an HF feed vaporizer, an HF superheater, an acid scrubber, a product drier, and a product collection system.

As in Example 1, the reactor is heated to a temperature of about 180° C. with a $N_2$ purge going over the catalyst after the reactor is installed in a constant temperature sand bath. HF feed is introduced to the reactor (via the vaporizer and superheater) as a co-feed with the $N_2$ for 15 minutes when the $N_2$ flow was stopped. The HF flow rate is adjusted to 1.9 lb/hr and then ambient temperature 1,1,2,3-tetrachloropropene (1230xa) feed is started to the reactor via the nozzle at the top of the reactor. The feed rate of 1230xa is kept steady at 1.0 lb/hr and HF feed is kept steady at 1.9 lb/hr for about a 17 to 1 mole ratio of HF to 1230xa. Once the reaction starts the catalyst bed temperature rises to about 200° C. Initially the 1230xa conversion is 100% and the 1233xf selectivity is >97%. The reaction temperature is gradually increased as catalyst deactivation occurs to maintain a desired product collection rate, and reaction is stopped once the reaction temperature reaches 300° C. and the conversion of 1230xa is <30%. The reaction pressure is kept constant at 70 psig during the entire course of reaction. The reaction is continuously run for about 800 hours, a 36% longer run than the old reactor design.

The catalyst is then regenerated using oxygen and high temperature to burn off the coke that has coated the surface of the catalyst. The reaction is restarted as before and the catalyst has regained its activity. 1230xa conversion is once again 100% and 1233xf the selectivity is >97% at a catalyst bed hot spot temperature of 200° C. and at a pressure of 70 psig.

What is claimed is:

1. A process to prepare 2-chloro-3,3,3-trifluoropropene (1233xf) comprising:
    a) atomizing a starting composition comprising at least one compound having a structure selected from Formula I, II and II:

$$CX_2=CCl-CH_2X \quad \text{(Formula I)}$$

$$CX_3-CCl=CH_2 \quad \text{(Formula II)}$$

$$CX_3-CHCl-CH_2X \quad \text{(Formula III)}$$

wherein X is independently selected from F, Cl, Br and I, provided that at least one of X is not F;
    b) feeding said atomized starting composition into a fluorination reactor and contacting the atomized composition with superheated HF in said reactor to form a vaporized starting composition, which contacts a fluorination catalyst under conditions effective to form 1233xf.

2. The process of claim 1 wherein the vapor phase fluorination catalyst is selected from the group consisting of $Cr_2O_3$, $FeCl_3/C$, $Cr_2O_3/Al_2O_3$, $Cr_2O_3/AlF_3$, $Cr_2O_3$/carbon, $CoCl_2/Cr_2O_3/Al_2O_3$, $NiCl_2/Cr_2O_3/Al_2O_3$, $CoCl_2/AlF_3$, $NiCl_2/AlF_3$, and mixtures thereof.

3. The process of claim 1 wherein the contacting of step (b) occurs substantially instantaneously with formation of the vaporized starting composition.

4. A process to prepare 2,3,3,3-tetrafluoropropene (1234yf) comprising:
    a) providing a first intermediate composition comprising 2-chloro-3,3,3-trifluoropropene (1233xf) as prepared according to claim 1;
    b) contacting said first intermediate composition comprising 1233xf with HF in the presence of a fluorination catalyst under conditions effective to produce a second intermediate composition comprising 244bb; and
    c) dehydrochlorinating at least a portion of said 244bb to produce a reaction product comprising 1234yf.

5. The process according to claim 1 wherein HF and the starting composition have a residence time in a heating chamber of no greater than about 1 second wherein said reactor is comprised of a heating chamber.

6. The process according to claim 1 wherein the starting composition comprises a compound selected from the group consisting of 1,1,2,3,tetrachloropropene, 1,1,1,2,3-pentachloropropane, 2,3,3,3-tetrachloropropene and combination thereof.

7. The process according to claim 1 wherein the starting composition is atomized proximate the catalyst.

8. The process according to claim 1 wherein the starting composition is atomized by passing it through an atomizing nozzle exiting into the reactor, the nozzle located proximate to the catalyst.

* * * * *